United States Patent [19]

Plass et al.

[11] Patent Number: 5,074,851
[45] Date of Patent: Dec. 24, 1991

[54] OSTOMY BAG INCLUDING A MULTIPLE LAYER FILTER

[75] Inventors: Ronald A. Plass, Lindfield; Gerald T. Whiting; Peter L. Steer, both of East Grinstead, all of England

[73] Assignee: E. R. Squibb & Sons, Inc., Princeton, N.J.

[21] Appl. No.: 547,422

[22] Filed: Jul. 3, 1990

Related U.S. Application Data

[63] Continuation of Ser. No. 320,186, Mar. 6, 1989, abandoned.

[30] Foreign Application Priority Data

Mar. 7, 1988 [GB] United Kingdom ............... 8805361
Apr. 19, 1988 [GB] United Kingdom ............... 8809222

[51] Int. Cl.[5] ............................................. A61F 5/44
[52] U.S. Cl. ................................ 604/333; 55/385.4; 55/387
[58] Field of Search ........ 604/277, 317, 327, 332–345; 55/316, 318, 320, 321, 527, 528, 385.4, 387

[56] References Cited

U.S. PATENT DOCUMENTS

| | | |
|---|---|---|
| 3,575,170 | 4/1971 | Clark . |
| 3,759,260 | 9/1973 | Nolan et al. . |
| 3,804,091 | 4/1974 | Nolan et al. . |
| 3,952,727 | 4/1976 | Nolan . |
| 4,120,715 | 10/1978 | Ockwell et al. . |
| 4,181,513 | 1/1980 | Fukuda et al. ......................... 55/528 |
| 4,203,445 | 5/1980 | Jessup et al. . |
| 4,274,848 | 6/1981 | La Gro . |
| 4,318,406 | 3/1982 | McLeod . |
| 4,411,659 | 10/1983 | Jensen et al. . |
| 4,460,392 | 7/1984 | Poulsen et al. ....................... 604/333 |
| 4,668,258 | 5/1987 | Steer ...................................... 55/528 |
| 4,723,951 | 2/1988 | Steer ...................................... 604/333 |

FOREIGN PATENT DOCUMENTS

| | | |
|---|---|---|
| 631987 | 6/1968 | Canada . |
| 235928 | 10/1987 | European Pat. Off. ............ 604/333 |
| 3237127 | 4/1984 | Fed. Rep. of Germany ...... 604/317 |
| 1117204 | 6/1968 | United Kingdom . |
| 1449119 | 11/1972 | United Kingdom .................. 55/316 |
| 1595906 | 8/1981 | United Kingdom . |
| 1596047 | 8/1981 | United Kingdom . |
| 2139501 | 11/1984 | United Kingdom ................ 604/332 |
| 2177604 | 1/1987 | United Kingdom ................ 604/332 |

*Primary Examiner*—John D. Yasko
*Assistant Examiner*—Anthony Gutowski
*Attorney, Agent, or Firm*—Robert E. Lee

[57] ABSTRACT

A bag or pouch for receiving discharge from the human body is made of two superposed sheets of synthetic plastics material joined around their edges and has a filter attached to an upper part of an interior surface of one of the walls, there being a hole or slit in the wall to allow gases exiting the filter to pass to the exterior of the bag or pouch, and an intervening wall is included to separate the filter region from the remainder of the interior of the bag or pouch, said wall being characterized by having a series of scattered holes therein, there being from 100 to 300 holes per square inch (155000 to 465000 holes per square meter) and each hole having a maximum dimension of from 130 to 340 microns. A filter is disclosed for use with the bag which includes the following components laminated together in the following order:

(a) a layer of hot-melt adhesive whereby the filter may be affixed to a wall of the bag;
(b) a layer of microfine non-woven material;
(c) a matrix layer of hot melt adhesive;
(d) a filter member of carbon-impregnated polyurethane open cell foam;
(e) a matrix layer of hot-melt adhesive; and
(f) a layer of non-woven fabric.

4 Claims, 2 Drawing Sheets

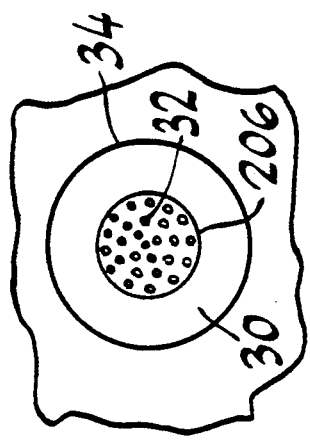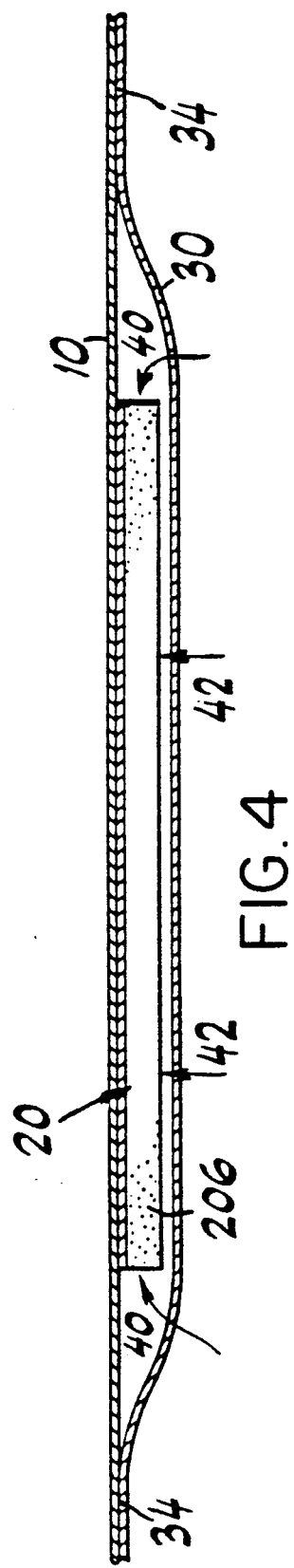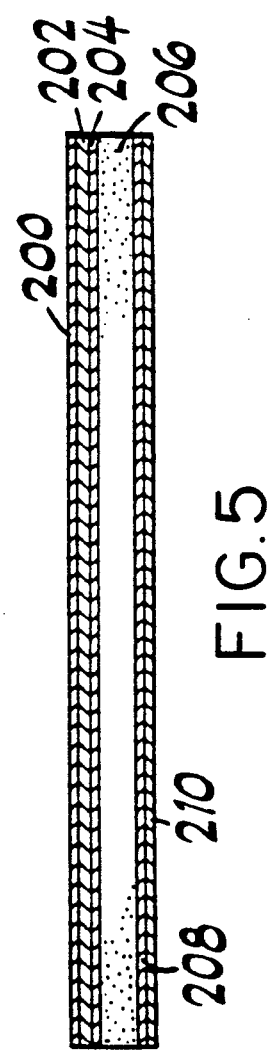

OSTOMY BAG INCLUDING A MULTIPLE LAYER FILTER

This is a continuation of Ser. No. 320,186 filed on Mar. 6, 1989, now abandoned.

BACKGROUND OF THE INVENTION

This invention relates to a bag or pouch including a filter and for receiving discharge from the human body. Examples of such bags or pouches are ostomy pouches and wound drainage bags.

The prior art is replete with designs of filters and with proposals for their inclusion in an ostomy bag, all directed at the problem of allowing escape of flatus gases from the bag while removing noxious-smelling components from such gases. Examples of proposals can be seen in U.K. Patent Nos. 1 117 204, 1 405 032, 1 462 492, 1 595 047, 1 595 906, 1 596 496, 2 036 564 and 2 059 797 and Canadian Patent 631 987, but there are many others. It has proved difficult to meet the important requirements of good filtering efficiency, comfort in wear, and minimum filter thickness. It will be appreciated that as an ostomy bag is worn under clothing, the bag plus filter desirably should be unobtrusive. Comfort in wear firstly requires flexibility of the filter as well as the bag and it is also desirable that the filter parts should be spaced from the tender stomal region. The present invention aims to solve or at least greatly mitigate these problems.

The present applicant has suggested in U.K. Patent No. 2 139 501 B that an ostomy bag particularly for ileostomy patients should be constructed with an intervening wall dividing the bag into two chambers. The present invention improves upon this concept by providing an intervening wall of a particularly advantageous nature.

SUMMARY OF THE INVENTION

According to the present invention, a bag or pouch for receiving discharge from the human body is made of two superposed sheets of synthetic plastics material joined around their edges and has a filter attached to an upper part of an interior surface of one of the walls, there being a hole or slit in the wall to allow gases exiting the filter to pass to the exterior of the bag or pouch, and an intervening wall is included to separate the filter region from the remainder of the interior of the bag or pouch, said intervening wall being characterized by having a series of scatter holes therein, there being from 100 to 300 holes per square inch (155000 to 465000 holes per square meter) and each hole having a maximum dimension of from 130 to 340 microns.

It has been surprisingly found that these values allow fully adequate flow of gas from the bag interior to the filter region and yet do not permit any substantial wetting of the filter, or clogging of the filter by body exudations such as fecal slurry.

It is preferred that each hole is substantially circular, and that the holes should be substantially uniformly spaced over the whole of the intervening wall.

The filter preferably (but not necessarily) includes the following components laminated together in the following order:

(a) a layer of hot-melt adhesive whereby the filter may be affixed to a wall of the bag;
(b) a layer of microfine non-woven material;
(c) a matrix layer of hot melt adhesive;
(d) a filter member of carbon-impregnated polyurethane open cell foam;
(e) a matrix layer of hot melt adhesive; and
(f) a layer of non-woven fabric.

The filter is, as stated, disposed in the space defined between the bag wall and the intervening wall. Preferably, the bag wall has an S-shaped cut therein to allow exit of flatus gases, located substantially at a central region of the filter. The intervening wall in use serves to permit the passage of flatus gases from bag interior to filter but substantially prevent passage of liquids or solids.

As an alternative, any suitable filter may be used.

The layer of non-woven fabric in the preferred filter has an air permeability in the range 0.25–1.0 c.c./cms$^2$/sec at 10 mm water pressure guage (W.P.G.), and has a weight of 64 gm/m$^2$ plus or minus 10%. The resulting laminated filter assembly has been found to have excellent deodorizing properties as well as high transmissibility to gas. In an H$_2$S deodorization test, a fully satisfactory deodorization was achieved with a flow of over 9 liters in 45 minutes.

BRIEF DESCRIPTION OF THE DRAWINGS

The invention will be better understood from the following description of a particular embodiment thereof, given with references to the accompanying illustrative and non-limiting drawings, in which:

FIG. 4 is a cross-section through part of the non-body side wall of the ostomy bag shown in FIGS. 1-3, illustrating the filter and the intervening wall;

FIG. 5 is an enlarged cross-sectional view of the filter showing its laminated construction; and FIG. 6 is an elevational plan view of the intervening wall showing a series of scattered holes therein.

DETAILED DESCRIPTION OF THE DRAWINGS

Figure 1:
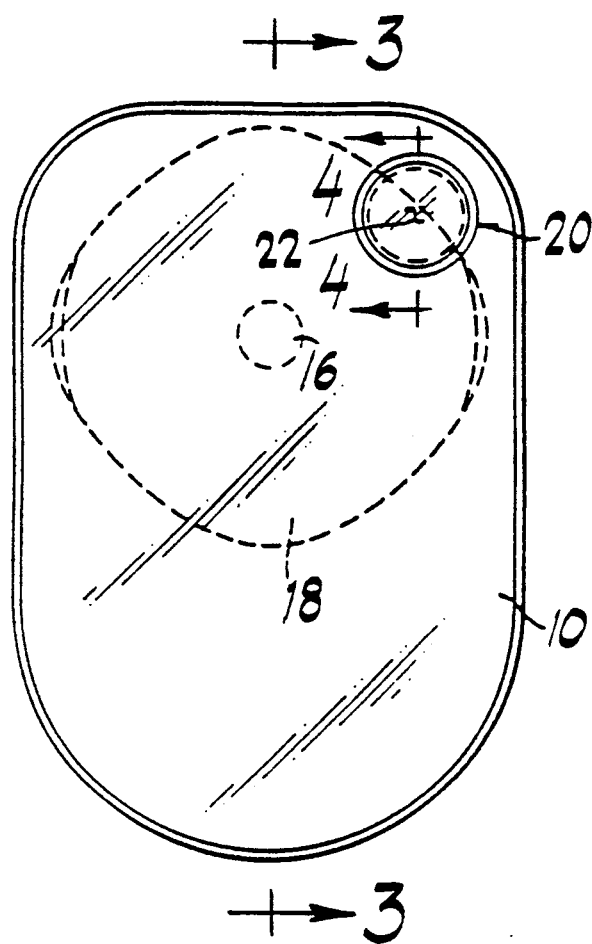
FIG. 1 is a front view of one embodiment of an ostomy bag according to the invention.
Figure 2:
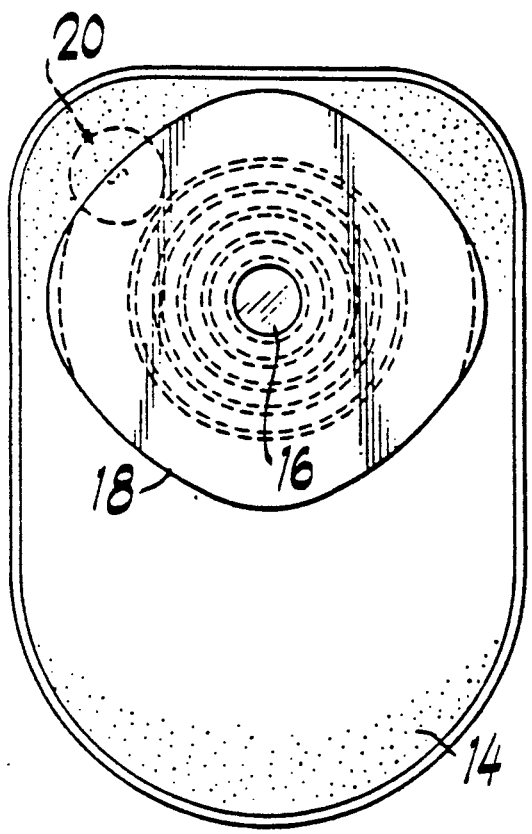
FIG. 2 is a rear view (i.e, looking directly at the body-side of the bag) of the bag shown in FIG. 1.
Figure 3:
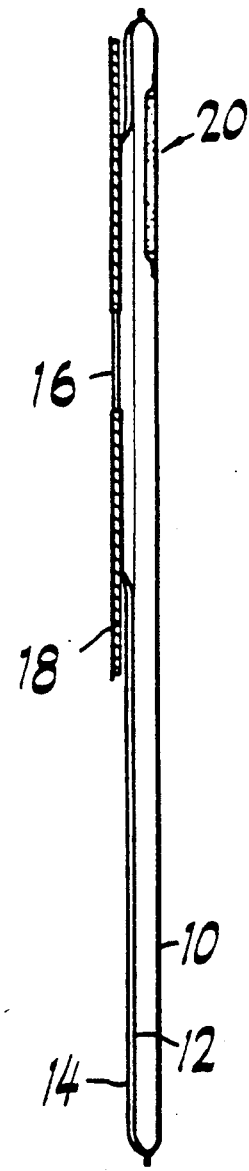
FIG. 3 is a diagrammatic cross-section of the bag shown in FIGS. 1 and 2 taken along the lines and arrows 3—3 in FIG. 1.

Referring firstly to FIGS. 1 to 3 the illustrated ostomy bag is largely conventional and comprises front and rear panels 10, 12 of synthetic plastics material joined around their edge by any suitable plastics welding or joining technique to constitute an ostomy bag. In addition, to give comfort and a warm feel to the skin, a needled film 14 overlays the rear bag wall. A stomal orifice 16 (FIG. 2) extends through the needled film and the rear bag wall and a pad 18 of medical grade adhesive, having thereon a polyethylene layer, is included so that the ostomy bag can be stuck to the body of the wearer in conventional manner. The adhesive surface of this medical grade pad is exposed by pulling off a protective layer of release paper. Suitable medical grade adhesive compositions are pressure sensitive adhesive formulations that consist of a homogenous blend of one or more water soluble or water swellable hydrocolloids dispersed in a viscous elastomeric substance such as polyisobutylene as disclosed by Chen in U.S. Pat. No. 3,339,546. Optionally, the adhesive composition can also include one or more cohesive strengthening agents as described by Chen et al. in U.S. Pat. No. 4,192,785 or one or more hydratable natural or synthetic polymers as described by Pawelchak et al. in U.S. Pat. No. 4,393,080. Preferably, the adhesive pad includes a thin water insoluable polymeric film such as polyethylene.

As will be seen in FIGS. 1 and 2 a filter assembly 20 is located at an upper corner of the bag and the bag wall 10 has therein an S-shaped cut 22 located substantially centrally of the filter assembly 20.

Referring now to FIGS. 4 and 5, although the filter assembly is seen as circular in these Figures, clearly this is not essential. It could be oval or rectangular or any other convenient shape. The illustrated filter assembly includes the following layers, and is attached to the inside surface of the bag front wall 10. The layers are listed in the order moving from the bag wall towards the interior of the bag, and comprise:

(a) a layer 200 of hot melt adhesive whereby the filter may be affixed to the wall of the bag;
(b) a layer 202 of microfine non-woven material; trade name LUTROVIL 708 is particularly suitable;
(c) a matrix layer 204 of hot melt adhesive;
(d) a filter disc 206, preferably 2 mm thick, of carbon-impregnated crushed polyurethane open cell foam;
(e) a matrix layer 208 of hot melt adhesive and
(f) a layer 210 of non-woven fabric.

The hot melt adhesive used in the layers 00, 204 and 208 comprise an ethylene vinyl acetate (EVA) adhesive. The matrix layers 204 and 208 are formed from strands or strings of the adhesive criss crossing the layer like a spider web.

Not connected to the filter, but connected to the bag wall by a closed loop weld 34 entirely surrounding the filter, is an intervening wall 30. This is preferably made of EBA (ethylene butylacrylate) synthetic plastics material 50 microns thick, needled at about 160 holes per square inch, that is, about 248000 holes per square meter. One may employ from about 155000 to 465000 holes per square meter (100 to 300 holes per square inch) or, more preferably, from about 186000 to 310000 holes per square meter (120 to 200 holes per square inch). The holes 32 are preferably substantially circular, though this is not absolutely essential. The maximum dimension of each hole may be from 75 to 300 microns, preferably 100 to 250 microns, and more preferably 110 to 240 microns. The purpose of the intervening wall 30 is to permit gas flow therethrough but substantially prevent any liquid or solid bag contents coming into contact with the filter.

The layers 202-210 specified above are integrated into a filter assembly by heat and pressure, following which the filter assembly is attached to the interior surface of the bag wall by suitably activating, by heating the adhesive layer 200. One suitable material for the layer 202 is a polypropylene microfine non-woven film. A suitable film of this type is known under the trade name LUTROVIL 708 A suitable material for the layer 210 is a gas-permeable non-woven synthetic plastics material known by the designation V115/463 from the manufacturer, Freudenberg U.K. Ltd, England.

This ostomy bag/filter design provides for a more efficient filter since gas existing in the bag flows through two different paths through the filter. Gas passing through the layer 30 into the region where the filter 20 is located will enter the filter disc 206 through the periphery and travel radially along the arrows 40 through the disc to its center to exit through the slit or opening 22. At the same time since the layer 210 of non-woven fabric is selectively gas permeable, gas can pass directly through the layer 210 and the disc 206 along the arrows 42 to exit the opening or slit 22. If the layer 210 did not offer any resistance to gas flow then the gas would take the path of least resistance and would pass mainly axially through the disc and not along the longer radial path reducing the efficiency of the filter. It has been found that by restricting free flow but allowing some flow (e.g. 0.25-1.0 c.c/cms$^2$/sec at 10 mm W.P.G) some of the gas will flow axially through the disc, about ⅓, while the remaining gas flows radially through the disc. This uses more of the filter disc material.

The non-woven layer of material 202 is also gas permeable but with some restricted flow. This restricted flow prevents gas from exiting too quickly insuring that the gas stay in contact with the filter disc for a minimum residence time.

By adopting this design, a satisfactory filter securely attached within an ostomy bag can be provided, the overall thickness of the bag in the filter region being well under 2½ mm. Moreover, both filter and bag are flexible and are unobtrusive even when worn under thin clothing. The bag and filter are also flexible and tend to follow the contours of the wearer's body.

As an advantageous feature to enhance the overall flexibility of the bag, the backing film on the medical grade adhesive is preferably embossed polyethylene. A film embossed with grooves is particularly preferred. A groove height and width of the order of around one-tenth of a millimeter may be employed.

Another advantageous feature of the illustrated design is that the medical grade adhesive may have thereon a sheet of paper carrying dimensioned circles as a guidance for the user when cutting a stomal orifice of the appropriate diameter in the medical grade adhesive pad. The adhesive is covered with a layer of release paper. The release paper is made to project slightly beyond the medical grade adhesive at regions located, for example, at the two ends of a horizontal diameter, such projection being for example about 2 or 3 mm. beyond the adhesive. These projections form an easily gripped tab to facilitate the peeling off of the release sheet carrying the stomal diameter diagrams once the necessary hole has been cut by scissors by the wearer in the conventional manner.

What is claimed is:

1. A bag or pouch for receiving discharge from the human body comprising:
   two superposed sheets of synthetic material joined around their edges; and
   a filter attached to an upper part of an interior surface of one of the sheets, there being a hole or slit in one sheet to allow gases exiting the filter to pass to the exterior of the bag or pouch, said filter including the following components laminated together in the following order:
   (a) a layer of hot-melt adhesive whereby the filter may be affixed to one sheet of the bag;
   (b) a layer of polypropylene microfine non-woven material which is gas permeable but with some restricted flow which prevents gas from exiting too quickly;
   (c) a matrix layer of hot-melt adhesive;
   (d) a filter member of carbon impregnated polyurethane open cell foam;
   (e) a matrix layer of hot melt adhesive; and (f) a layer of non-woven fabric which is selectively gas permeable so that gas flows both axially and radially through said filter.

2. A bag or pouch according to claim 1 in which the one sheet has an S-shaped cut therein to allow exit of the flatus gases, located substantially at a central region of the filter.

3. A bag or pouch for receiving discharge from the human body comprising:

two superposed sheets of synthetic plastics material joined around their edges;

a filter attached to an upper part of an interior surface of one of the sheets, there being a hole or slit in the one sheet to allow gases exiting the filter to pass to the exterior of the bag pouch, said filter including the following components laminated together in the following order:

(a) a layer of hot-melt adhesive whereby the filter may be affixed to the one sheet of the bag;

(b) a layer of microfine non-woven material which is partially restrictive to gas flow therethrough;

(c) a matrix layer of hot-melt adhesive;

(d) a filter member of carbon-impregnated polyurethane open cell foam;

(e) a matrix layer of hot melt adhesive; and (f) a layer of non-woven fabric which is partially restrictive to gas flow; and said bag or pouch further comprising:

an intervening wall included to separate the filter region from the remainder of the interior of the bag or pouch, said intervening wall being characterized by having a series of scatter holes therein, there being from 100 to 300 holes per square inch (155000 to 465000 holes per square meter) and each hole having a maximum dimension of from 130 to 340 microns.

4. A bag or pouch according to claim 1 in which the one sheet has an S-shaped cut therein to allow exit of the flatus gases, located substantially at a central region of the filter.

* * * * *